United States Patent
Yu et al.

(10) Patent No.: US 8,273,402 B2
(45) Date of Patent: Sep. 25, 2012

(54) DRUG COATED STENT WITH MAGNESIUM TOPCOAT

(75) Inventors: Eric Yu, Moraga, CA (US); James Mitchell, Windsor, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1308 days.

(21) Appl. No.: 11/678,676

(22) Filed: Feb. 26, 2007

(65) Prior Publication Data

US 2008/0208313 A1    Aug. 28, 2008

(51) Int. Cl.
*A61L 33/00* (2006.01)

(52) U.S. Cl. ...... 427/2.1; 623/1.39; 623/1.42; 623/1.11; 623/1.46; 427/2.25; 604/523; 424/423

(58) Field of Classification Search ............... 623/1.39, 623/1.15, 1.1, 1.11, 1.46, 1.42; 427/2.25; 424/423

See application file for complete search history.

(56) References Cited

U.S. PATENT DOCUMENTS

| | | | |
|---|---|---|---|
| 6,099,563 A | 8/2000 | Zhong | |
| 6,231,600 B1 | 5/2001 | Zhong | |
| 6,656,517 B2 | 12/2003 | Michal et al. | |
| 6,692,772 B2 | 2/2004 | Kaul et al. | |
| 2004/0267352 A1* | 12/2004 | Davidson et al. | 623/1.15 |
| 2005/0112170 A1* | 5/2005 | Hossainy et al. | 424/423 |
| 2005/0131513 A1* | 6/2005 | Myers | 623/1.11 |
| 2006/0276884 A1* | 12/2006 | Lye et al. | 623/1.39 |
| 2007/0043418 A1 | 2/2007 | Lee et al. | |
| 2008/0147177 A1* | 6/2008 | Scheuermann et al. | 623/1.42 |

FOREIGN PATENT DOCUMENTS

| | | |
|---|---|---|
| DE | 10361941 | 7/2005 |
| JP | 61249467 * | 6/1986 |
| WO | WO 2006/108065 | 10/2006 |
| WO | WO 2007/125532 | 11/2007 |

* cited by examiner

*Primary Examiner* — David Turocy
*Assistant Examiner* — Andrew Bowman (57) ABSTRACT

A method for manufacturing a drug carrying stent includes applying at least a first therapeutic agent to at least an outer portion of a stent framework and applying a first magnesium coating on at least a first portion of the applied first therapeutic agent.

16 Claims, 5 Drawing Sheets

DRUG COATED STENT WITH MAGNESIUM TOPCOAT

TECHNICAL FIELD

This invention relates generally to medical devices for treating vascular problems, and more particularly to a drug coated stent with a magnesium topcoat.

BACKGROUND OF THE INVENTION

Drug eluting stents have become popular medical devices. One difficulty with such devices is the difficulty in binding the drug to the stent and controlling drug elution. Previously, this problem has been addressed by incorporating the drug, often rapamycin, sirolimus, or the like, within a polymer and layering the drug polymer on a stent surface.

The polymer coating process generally requires a solvent, in which the drugs are usually soluble, and thus limits the ability to control elution of one or more therapeutic agents. It is therefore desirable to provide a drug coated stent without polymeric vehicles to deliver the drug.

The biocompatibility of polymers has come into question. A degradable coating may provide biocompatibility advantages over permanent polymer coatings in allowing the tissue to eventually come into direct contact with the bulk stent material.

Polymer coatings commonly have problems with durability, which may put patients at risk of embolism, and also prevent their use on self-expanding stent platforms.

Polymer coatings face limitations of elution control. It is therefore desirable to have a coating with improved elution control.

It would be desirable, therefore, to provide a substantially polymer-free drug coated stent that would overcome the limitations and disadvantages inherent in the devices described above.

SUMMARY OF THE INVENTION

A first aspect of the invention provides a method for manufacturing a drug carrying stent. The method includes applying at least a first therapeutic agent to at least an outer portion of a stent framework and applying a first magnesium coating on at least a first portion of the applied first therapeutic agent.

Another aspect of the invention provides a system for treating a vascular condition. The system includes a catheter and a stent disposed on the catheter. The stent includes a therapeutic agent applied on at least a portion of the stent framework and a magnesium coating disposed on the applied therapeutic agent.

Another aspect of the invention provides a stent including a stent framework, a therapeutic agent applied on at least a portion of the stent framework, and a magnesium coating disposed on the applied therapeutic agent.

The present invention is illustrated by the accompanying drawings of various embodiments and the detailed description given below. The drawings should not be taken to limit the invention to the specific embodiments, but are for explanation and understanding. The detailed description and drawings are merely illustrative of the invention rather than limiting, the scope of the invention being defined by the appended claims and equivalents thereof. The drawings are not to scale. The foregoing aspects and other attendant advantages of the present invention will become more readily appreciated by the detailed description taken in conjunction with the accompanying drawings.

DETAILED DESCRIPTION

The invention will now be described by reference to the drawings wherein like numbers refer to like structures.

Figure 1:
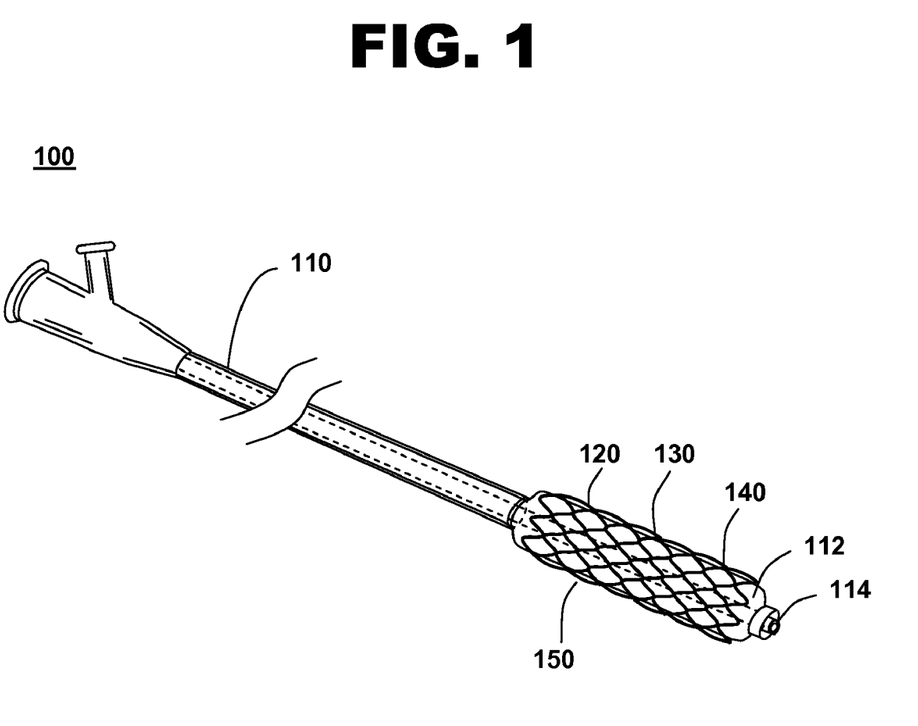
FIG. 1 is an illustration of a system for treating a vascular condition including a drug coated stent coupled to a catheter, in accordance with one embodiment of the current invention.

FIG. 1 shows an illustration of a system for treating a vascular condition, comprising a drug coated stent coupled to a catheter, in accordance with one embodiment of the present invention at 100. Coated stent with catheter 100 includes a drug coated stent 120 coupled to a delivery catheter 110. Drug coated stent 120 includes a stent framework 130 and a drug coating 140 disposed on the stent framework and a magnesium coating 150. Drug coating 140 includes at least a first therapeutic agent. In certain embodiments, drug coating 140 includes at least two therapeutic agents—a first therapeutic agent and a second therapeutic agent for example.

Insertion of coated stent 120 into a vessel in the body helps treat, for example, heart disease, various cardiovascular ailments, and other vascular conditions. Catheter-deployed coated stent 120 typically is used to treat one or more blockages, occlusions, stenoses, or diseased regions in the coronary artery, femoral artery, peripheral arteries, and other arteries in the body. Treatment of vascular conditions may include the prevention or correction of various ailments and deficiencies associated with the cardiovascular system, the cerebrovascular system, urinogenital systems, biliary conduits, abdominal passageways and other biological vessels within the body.

An exemplary drug coating 140 includes or encapsulates one or more therapeutic agents. Drug coating 140 may comprise one or more therapeutic agents dispersed within or encased by drug layers or barrier layers, such as an intermediate layer of magnesium, on coated stent 120, which are eluted or leached from coated stent 120 with, for example, controlled time delivery after deployment of coated stent 120 into the body. A therapeutic agent is capable of producing a beneficial effect against one or more conditions including coronary restenosis, cardiovascular restenosis, angiographic restenosis, arteriosclerosis, hyperplasia, and other diseases or conditions. For example, the therapeutic agent can be selected to inhibit or prevent vascular restenosis, a condition corresponding to a narrowing or constriction of the diameter of the bodily lumen where the stent is placed. Drug coating 140 may comprise, for example, an antirestenotic agent such as rapamycin, a rapamycin derivative, or a rapamycin analog to prevent or reduce the recurrence of narrowing and blockage of the bodily vessel. Drug coating 140 may comprise an anti-cancer drug such as camptothecin or other topoisomerase inhibitors, an antisense agent, an antineoplastic agent, an antiproliferative agent, an antithrombogenic agent, an anticoagulant, an antiplatelet agent, an antibiotic, an anti-inflammatory agent, a steroid, a gene therapy agent, an organic drug, a pharmaceutical compound, a recombinant DNA product, a recombinant RNA product, a collagen, a collagenic derivative, a protein, a protein analog, a saccharide, a saccharide derivative, a bioactive agent, a pharmaceutical drug, a therapeutic substance, or a combination thereof. In one example, a first therapeutic agent comprises an antirestenotic drug such as rapamycin, a rapamycin derivative, or a rapamycin analog. The second therapeutic agent may comprise, for example, an anti-cancer drug such as camptothecin or other topoisomerase inhibitors. The therapeutic agent constituency in the drug layers may be, for example, between 0.1 percent and 50 percent of the drug layer by weight. In another example, the first therapeutic agent comprises an anti-proliferative compound such as 5-fluorouracil, with an optional second therapeutic agent such as rapamycin, a rapamycin derivative, a rapamycin analog, or dexamethosone. In another example, the first therapeutic agent comprises an anti-inflammatant such as dexamethasone, and an optional second therapeutic agent such as 5-fluorouracil.

In one example, a first therapeutic agent comprises an antirestenotic drug such as rapamycin, a rapamycin derivative, or a rapamycin analog. The second therapeutic agent may comprise, for example, an anti-cancer drug such as camptothecin or other topoisomerase inhibitors. The therapeutic agent constituency in the drug layers may be, for example, between 0.1 percent and 50 percent of the drug layer by weight. In another example, the first therapeutic agent comprises an anti-proliferative compound such as 5-fluorouracil, with an optional second therapeutic agent such as rapamycin, a rapamycin derivative, a rapamycin analog, or dexamethosone. In another example, the first therapeutic agent comprises an anti-inflammatant such as dexamethasone, and an optional second therapeutic agent such as 5-fluorouracil.

The elution rates of the therapeutic agents and total drug eluted into the body and the tissue bed surrounding the stent framework are based on the target thickness of drug coating 140, the constituency and individual layer thicknesses of drug coating 140, the nature and concentration of the therapeutic agents, the thickness, composition, and degradation rate of any magnesium coat, the total number of layers of successive therapeutic and magnesium layers, and other factors. Drug coating 140 may include and elute or leach multiple therapeutic agents to achieve the desired therapeutic effect. The magnesium topcoat layer 150 is absorbed into the body. For example, in one embodiment, the magnesium layer successively degrades and the magnesium is absorbed into the body. In certain embodiments, a portion of the drug can diffuse through the magnesium layer, although the primary elution of drug only occurs after the magnesium layer/s leach off the stent framework.

Catheter 110 of an exemplary embodiment of the present invention includes a balloon 112 that expands and deploys the stent within a vessel of the body. After positioning coated stent 120 within the vessel with the assistance of a guide wire traversing through a guidewire lumen 114 inside catheter 110, balloon 112 is inflated by pressurizing a fluid such as a contrast fluid or saline solution that fills a tube inside catheter 110 and balloon 112. Coated stent 120 is expanded until a desired diameter is reached, and then the fluid is depressurized or pumped out, separating balloon 112 from coated stent 120 and leaving coated stent 120 deployed in the vessel of the body. Alternately, catheter 110 may include a sheath that retracts to allow expansion of a self-expanding version of coated stent 120.

Figure 2:
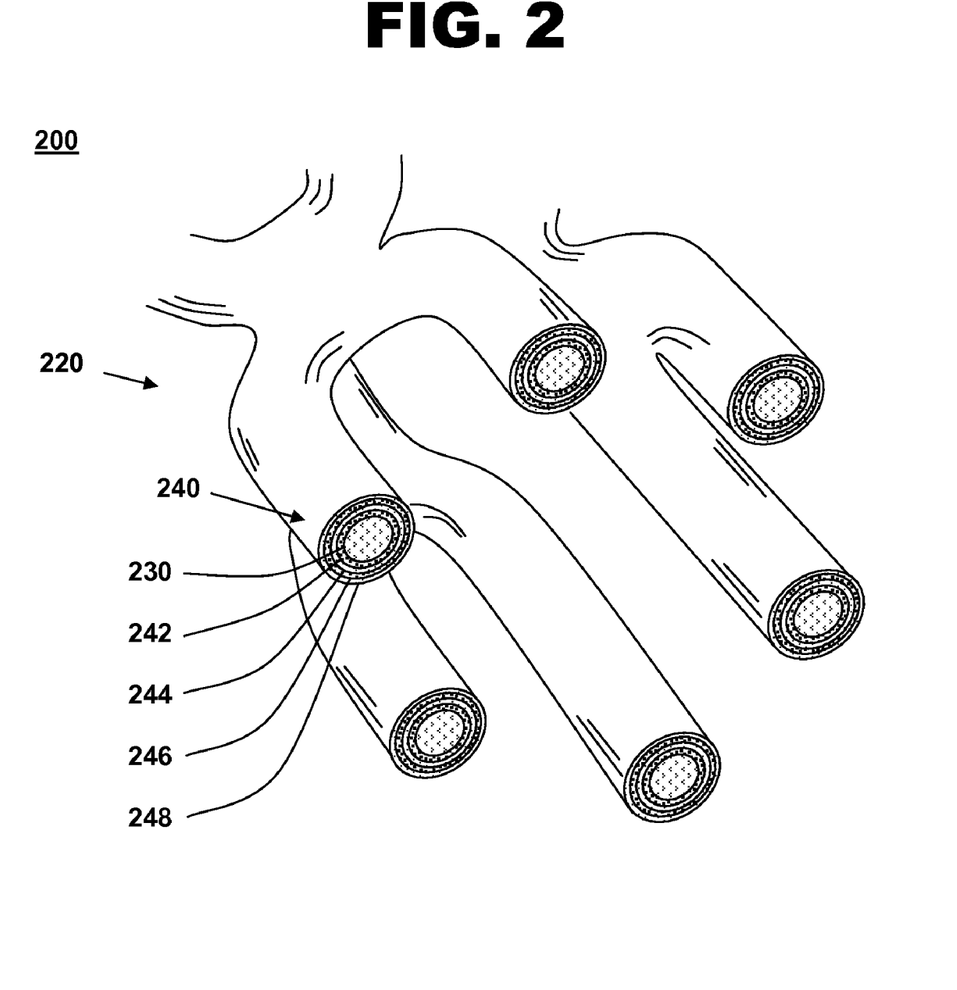
FIG. 2 is a cross-sectional perspective view of a drug coated stent, in accordance with one embodiment of the current invention.

FIG. 2 shows a cross-sectional perspective view of a drug coated stent, in accordance with one embodiment of the present invention at 200. A drug coated stent 220 includes a stent framework 230 with a drug coating 240 disposed on stent framework 230. In certain embodiments, drug coating 240 includes a plurality of thin drug layers 242 and 246 that are positioned between magnesium coating layers 244 and 248. Drug layers 242 and 246 include at least a first therapeutic agent, and magnesium coating layers 244 and 248 include magnesium. In one embodiment, the magnesium coating layers are sputter coats. In other embodiments, the magnesium coating is applied using another appropriate technique, such as vacuum deposition, electrolytic deposition, electroless deposition, electrostatic deposition, or the like. In one embodiment, the magnesium coating layer is a topcoat.

The magnesium coating layer is formed from dry magnesium powder or solid target, in one embodiment. In another embodiment, the magnesium is dispersed within a solvent solution.

Although illustrated with two sets of drug layers and magnesium coating layers, multiple sets of magnesium coating layers may be disposed on stent framework 230. For example, ten sets of layers, each layer on the order of 0.1 micrometers thick, can be alternately disposed on stent framework 230 to produce a two-micrometer thick coating. In another example, twenty sets of layers, each layer on the order of 0.5 micrometers thick, can be alternately disposed on stent framework 230 to produce a twenty-micrometer thick coating. The drug layers and the magnesium coating layers need not be the same thickness, and the thickness of each may be varied throughout drug coating 240. In one embodiment, the total quantity of magnesium is controlled to reduce potentially undesirable or toxic effects.

Stent framework 230 comprises a metallic base or a polymeric base, such as stainless steel, nitinol, tantalum, MP35N alloy, platinum, titanium, a chromium-based alloy, a suitable biocompatible alloy, a suitable biocompatible material, a biocompatible polymer, or a combination thereof. The polymeric base material may comprise any suitable polymer for biomedical stent applications, as is known in the art.

In one example, drug layers 242 and 246 comprise a first therapeutic agent such as camptothecin, rapamycin, a rapamycin derivative, or a rapamycin analog. Magnesium coating layers 244 and 248 comprise a magnesium layer of a predetermined thickness. In one embodiment, the thickness of the magnesium coating is selected based on expected degradation rates of the magnesium, while in other embodiments, the thickness is selected based on the drug maintained in place between the stent surface and the magnesium layer. In another embodiment, the thickness of the magnesium layer is variable over the length of the stent framework. For example, over one span of the stent framework, the magnesium layer is 2 micrometers thick, while in a second span of the stent framework, the magnesium layer is 4 micrometers thick. Drug or magnesium elution refers to the transfer of a therapeutic agent from drug coating 240 to the surrounding area or bloodstream in a body. The amount of drug eluted is determined as the total amount of therapeutic agent excreted out of drug coating 240, typically measured in units of weight such as micrograms, or in weight per peripheral area of the stent. In another embodiment, the concentration of the therapeutic agents in either drug layers 242 and 246 or barrier layers 244 and 248 are modulated to provide a predetermined drug-release profile.

Figure 3:
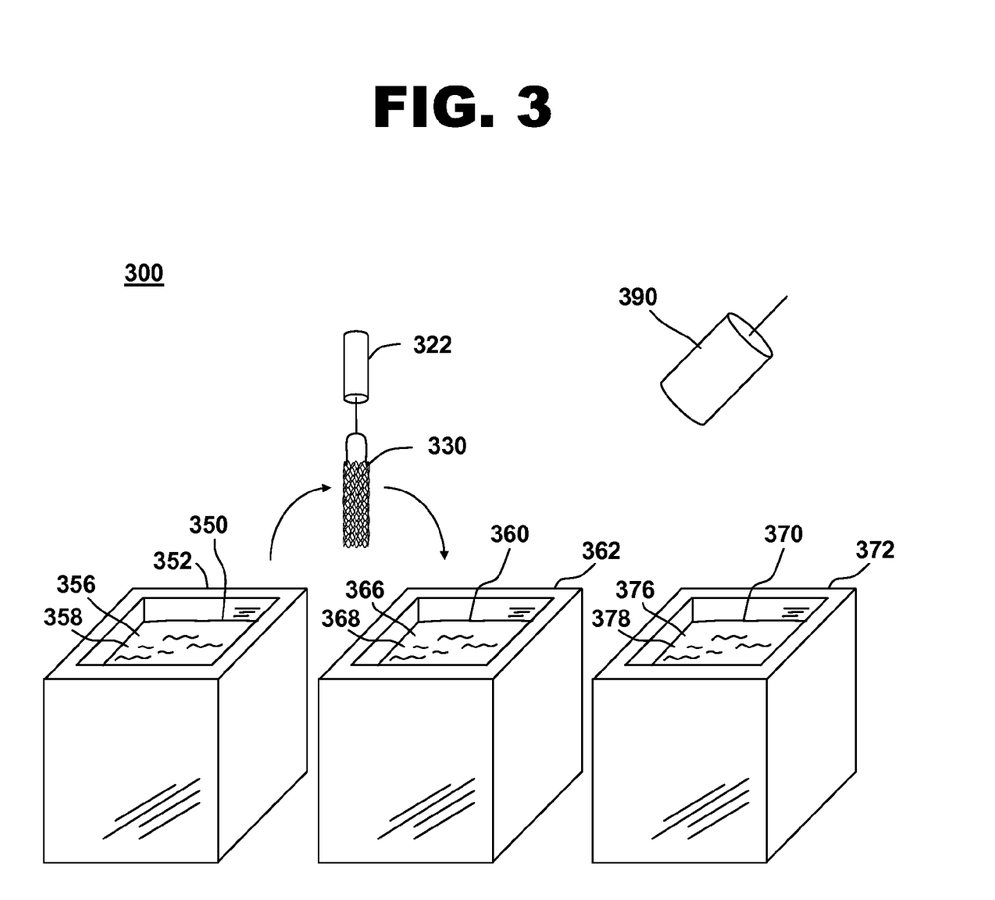
FIG. 3 is an illustration of a system for applying a drug coating on a stent, in accordance with one embodiment of the current invention.

FIG. 3 shows an illustration of an example system for applying a drug coating on a stent, in accordance with one embodiment of the current invention at 300. Drug coating system 300 includes a first solution 350 in a first tank 352, a second solution 360 in a second tank 362, and a mechanism 322 such as a mandrel, a clamp, or a tether for holding and transporting stents in and out of a tank either manually or automatically. Multiple stent frameworks 330 are readily accommodated for dipping and drying in a batch or continuous batch process.

For example, first solution 350 includes a first therapeutic agent 356, and a first solvent 358. Stent framework 330 can be dipped into first solution 350 and dried, for example, by positioning dipped stent framework 330 in air or in an oven and evaporating first solvent 358 to form a drug layer. Minimizing the solids content of first solution 350 can lower the viscosity, so that uniform coating and minimal or no bridging occurs across the apertures of stent framework 330. Alternatively, first solution 350 can be ultrasonically sprayed, electrostatically sprayed, or applied via micro-droplet deposition, supercritical fluids, focused acoustic beams, or piezo injectors.

After application of first layer of therapeutic agent, a layer of magnesium may be applied.

Second solution 360 includes second therapeutic agent and a second solvent 368. Stent framework 330 with the first laminated drug layer can be dipped into second solution 360 and dried, for example, by positioning dipped stent framework 330 in an oven or in air for high throughput and evaporating second solvent 368 to form a therapeutic agent layer. Second solution 360 may include a second therapeutic agent 366 dissolved into second solvent 368. Low viscosity for minimizing bridging and webbing across the apertures of stent framework 330 can be obtained by minimizing the solids content of second solution 360. Alternatively, second solution 360 can be ultrasonically sprayed, electrostatically sprayed, or applied via inkjet technology.

After application of first layer of therapeutic agent, a layer of magnesium may be applied.

A third solution 370 in a third tank 372 includes a third solvent 378 in certain embodiments. Third solution 370 may include a third therapeutic agent 376 dissolved in third solvent 378. In one example, third solvent 378 is the same as first solvent 358, and third therapeutic agent 376 is the same as first therapeutic agent 356, though at a higher or a lower concentration than first therapeutic agent 356 in first solution 350. In this case, the concentration of third therapeutic agent 376 disposed on stent framework 330 can be higher or lower than previously coated and dried drug layers. The concentration of first therapeutic agent 356 in the drug layers can be modulated to provide a predetermined drug-release profile.

In another example, third solvent 378 is the same as second solvent 368, and third therapeutic agent 376 is the same as second therapeutic agent 366 though at a higher or a lower concentration than second therapeutic agent 366 in second solution 360. The concentration of third therapeutic agent 376 disposed on stent framework 330 can be higher or lower than previously dipped and dried barrier layers, so that the concentration of second therapeutic agent 366 in the barrier layers can be modulated to provide a predetermined drug-release profile for second therapeutic agent 366 from a coated stent when deployed in a body.

In another example, more than one therapeutic agent may be formulated in each of the solutions and applied as specified in the aforementioned example.

In addition to the dipping tanks, the system further includes a magnesium deposition device 390, such as a sputter gun or nozzle. Device 390 is communicatively coupled to a source of magnesium for sputter coating the stent 330 with magnesium. Any appropriate commercially available sputtering device can be used. The device is used to apply a layer of magnesium to the at least a first surface of the stent.

Figure 4:
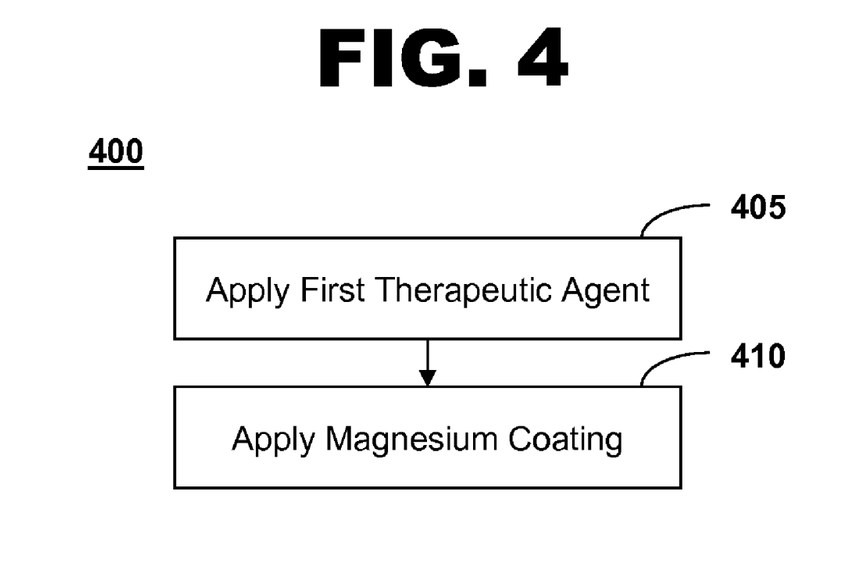
FIG. 4 is a flow diagram of a method of applying a drug-delivery coating on a stent, in accordance with one embodiment of the current invention

FIG. 4 shows a flow diagram of a method of applying a drug coating on a stent, in accordance with one embodiment of the present invention at 400. Drug application method 400 includes various steps to form a drug coating on a stent framework.

At least a first therapeutic agent is applied to at least an outer portion of a stent framework at block 405. In one embodiment, at least the first therapeutic agent is applied to an inner portion of the stent framework as well. The outer portion of the stent framework in any portion that contacts a vessel wall upon deployment within the body, and the inner portion of the stent framework is any portion of the stent framework that is subject to interaction with blood upon deployment within a body. In embodiments featuring application of more than one therapeutic agent, the therapeutic agents can be applied simultaneously, sequentially, or at different portions of the surface of the stent framework. In one embodiment, the stent framework is metallic, and the therapeutic agent is applied to the bare metal surface. The surface can include a variety of surface modifications, including pores, nanopores, pits, dips, channels, or the like. Alternately, the surface can be a smooth surface. In one embodiment, the surface is a polished surface.

Having applied the therapeutic agents to the stent framework, a first magnesium coating is applied to the applied therapeutic agents on at least a first portion of the stent framework, at block 410. The magnesium coating maintains the therapeutic agent(s) between the surface of the stent framework and the magnesium coating until the magnesium coating is degraded during implantation. The degradation of the magnesium coating, in one embodiment, has therapeutic effects, such as a reduction in proliferation. In one embodiment, the magnesium coating is applied as a sputter coat. In another embodiment, the magnesium coating is applied with vacuum deposition. In one embodiment, certain areas of the stent framework that are subject to increased mechanical strain, such as crowns, are masked during application of the magnesium coats. In another embodiment, either the stent or sputter nozzle is rotated to apply the sputter coat in a more uniformly distributed fashion. In other embodiments, multiple sputter layers of magnesium are applied to the stent. The sputter coat of magnesium, in one embodiment, is applied to result in a drug burst upon deployment so that a relatively large dose of therapeutic agent is released in the short term (such as the first hours or days of deployment). Alternatively, the magnesium layer can be sputter coated to result in a relatively slow drug release over a span of weeks after deployment. Both the concentration of magnesium and the thickness of the magnesium coating can be configured to obtain certain release characteristics.

Figure 5:
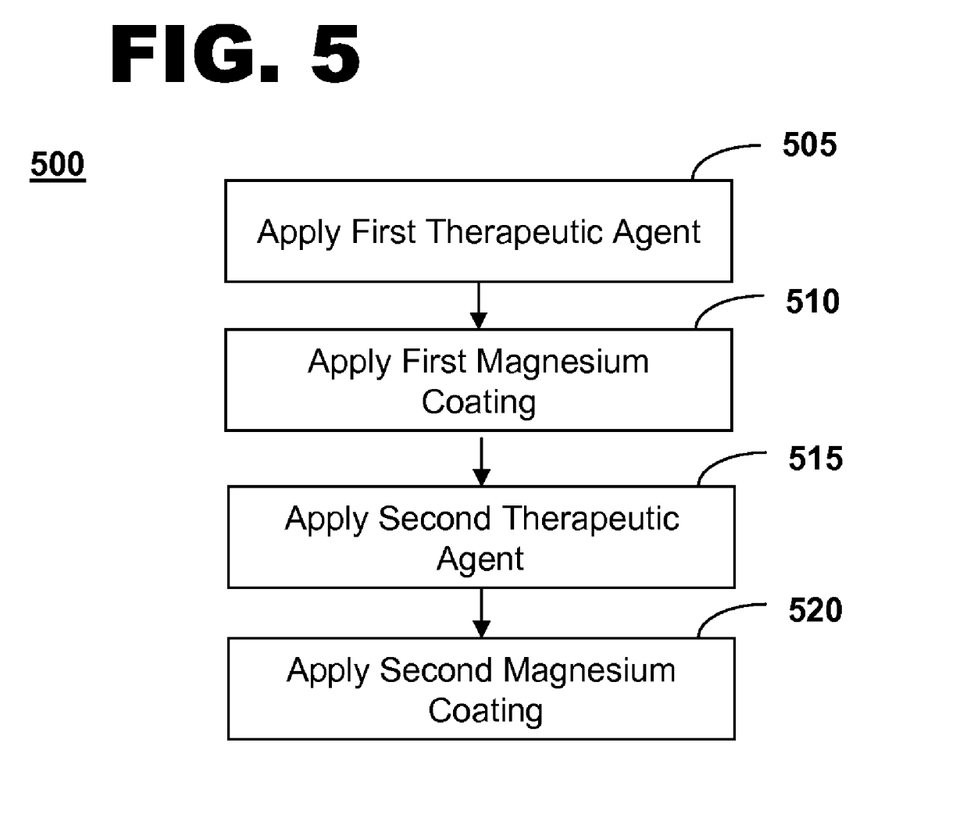
FIG. 5 is a flow diagram of a method of applying a drug-delivery coating on a stent, in accordance with one embodiment of the current invention.

FIG. 5 shows a flow diagram of a method of applying a drug coating on a stent, in accordance with one embodiment of the present invention at 500. Drug application method 500 includes various steps to form a drug coating on a stent framework.

At least one therapeutic agent is applied to at least an outer portion of a stent framework at block 505. In one embodiment, at least the first therapeutic agent is applied to an inner portion of the stent framework as well. The outer portion of the stent framework is any portion that contacts a vessel wall upon deployment within the body, and the inner portion of the stent framework is any portion of the stent framework that is subject to interaction with blood upon deployment within a body. In embodiments featuring application of more than one therapeutic agent, the therapeutic agents can be applied simultaneously, sequentially, or at different portions of the surface of the stent framework. For example, a first drug is applied along a first span of the stent framework, while a second drug is applied along a second span of the stent framework. In one embodiment, the stent framework is metallic, and the therapeutic agent is applied to the bare metal surface. The surface can include a variety of surface modifications, including pores, nanopores, pits, dips, channels, or the like. Alternately, the surface can be a smooth surface. In another embodiment the surface is nonporous.

Having applied the therapeutic agents to the stent framework, a first magnesium coating is applied to the applied therapeutic agents on at least a first portion of the stent framework at block 510. The magnesium coating maintains the therapeutic agent(s) between the surface of the stent framework and the magnesium coating until the magnesium coating is degraded when implanted. The degradation of the magnesium coating, in one embodiment, has therapeutic effects. In one embodiment, the magnesium coating is applied as a sputter coat. In another embodiment, the magnesium coating is applied with vacuum deposition.

A second layer of therapeutic agents, such as a second therapeutic agent is applied to the first magnesium coat at block 515. The second therapeutic agent can be the same as, or different from, the first therapeutic agent.

A second magnesium layer is applied to the second layer of therapeutic agent at block 520.

Figure 6:
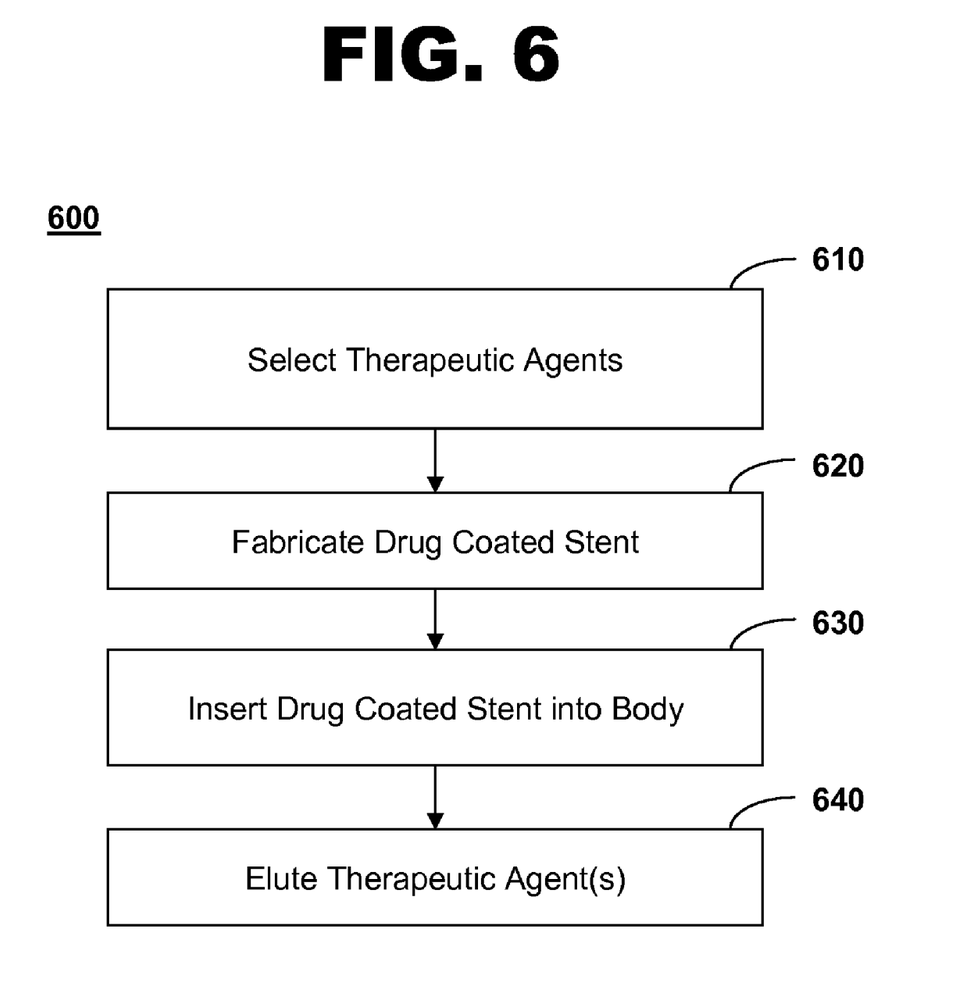
FIG. 6 is a flow diagram of a method for treating a vascular condition, in accordance with one embodiment of the current invention.

FIG. 6 shows a flow diagram of a method for treating a vascular condition, in accordance with one embodiment of the present invention at 600. Vascular condition treatment method 600 includes steps to insert a drug coated stent within a vessel of a body and to elute at least one therapeutic agent from the drug coated stent into the body. One or more therapeutic agents are included or interdispersed within thin drug layers and magnesium coating layers of the laminated drug stent coating.

At least a first therapeutic agent is selected at block 610. The concentrations of therapeutic agents are selected to provide desired pharmacological or therapeutic results.

A coated stent with a drug coating is fabricated by using selected therapeutic agents, solvents and concentrations thereof, as seen at block 620. The drug layers include a therapeutic agent applied directly to a bare metal stent.

When ready for deployment, the drug coated stent with the selected therapeutic agents is inserted into a vessel of the body, as seen at block 630. The drug coated stent is inserted typically in a controlled environment such as a catheter lab or hospital. A delivery catheter, which helps position the drug coated stent in a vessel of the body, is typically inserted through a small incision of the leg and into the femoral artery, and directed through the vascular system to a desired place in the vessel. Guide wires threaded through an inner lumen of the delivery catheter assist in positioning and orienting the drug coated stent. The position of the drug coated stent may be monitored, for example, with a fluoroscopic imaging system or an x-ray viewing system in conjunction with radiopaque markers on the coated stent, radiopaque markers on the delivery catheter, or contrast fluid injected into an inner lumen of the delivery catheter and into an inflatable catheter balloon that is coupled to the drug coated stent. The stent is deployed, for example, by expanding the stent with a balloon or by extracting a sheath that allows a self-expandable stent to enlarge after positioning the stent at a desired location within the body. Before clinical use, the stent is sterilized by using conventional medical means.

Once deployed, the therapeutic agents in the drug coating are eluted, as seen at block 640. The elution rates of the selected therapeutic agents into the body and the tissue bed surrounding the stent framework are based on the thickness of the drug layers and magnesium layers, and the concentration of the therapeutic agents contained therein, among other factors.

Although the present invention applies to cardiovascular and endovascular stents with timed-release therapeutic agents, the use of drug coatings may be applied to other implantable and blood-contacting biomedical devices such as coated pacemaker leads, microdelivery pumps, feeding and delivery catheters, heart valves, artificial livers and other artificial organs.

While the invention has been described with reference to particular embodiments, it will be understood by one skilled in the art that variations and modifications may be made in form and detail without departing from the spirit and scope of the invention.

What is claimed is:

1. A method for manufacturing a drug carrying stent, the method comprising:
   applying a first drug layer to at least an outer portion of a stent framework, the first drug layer being polymer-free and including one or more first therapeutic agents;
   applying a first magnesium coating layer on at least a portion of the first drug layer, the first magnesium coating layer consisting of magnesium;
   applying a second drug layer consisting of a second therapeutic agent on the first magnesium coating layer; and
   applying a second magnesium coating layer on the second drug layer.

2. The method of claim 1 wherein the applying a first drug layer to at least an outer portion of a stent framework includes applying a predetermined concentration of the one or more first therapeutic agents on the stent framework by a method selected from the group consisting of dipping, ultrasonic spraying, electrostatic spraying, and inkjet coating.

3. The method of claim 1 wherein the stent framework is substantially polymer-free.

4. The method of claim 1 wherein the stent framework is metallic, and wherein the one or more first therapeutic agents are applied to bare metal of the stent framework.

5. The method of claim 1 wherein the first magnesium coating layer is applied as a sputter coat.

6. The method of claim 1 wherein the first magnesium coating layer is applied with vacuum deposition.

7. The method of claim 1 wherein the second magnesium coating layer is a topcoat.

8. The method of claim 1 wherein the first therapeutic agent and the second therapeutic agent are different agents.

9. The method of claim 1 wherein the first therapeutic agent and the second therapeutic agent are substantially similar agents.

10. The method of claim 1 wherein the outer portion is a first portion of the stent framework, the method further comprising:
    applying a third therapeutic agent on at least a second portion of the stent framework, the portion being separate from the first portion.

11. A method of treating a vascular condition, the method comprising:
    selecting at least a first therapeutic agent;
    selecting at least a second therapeutic agent;

fabricating a drug coated stent, the fabricating the drug coated stent including:
   applying the selected first therapeutic agent to a stent framework to form a first drug layer, the first drug layer being polymer-free,
   covering the first drug layer with a first magnesium coating layer consisting of magnesium,
   applying the selected second therapeutic agent to the first magnesium coating layer to form a second drug layer, and
   covering the second drug layer with a second magnesium coating layer;
inserting the fabricated drug coated stent within a body;
eluting the second therapeutic agent from the drug coated stent within the body after the second magnesium coating layer covering the second therapeutic agent degrades; and
eluting the first therapeutic agent from the drug coated stent within the body after the first magnesium coating layer covering the first therapeutic agent degrades.

12. The method of claim 1 wherein the first drug layer consists of the one or more therapeutic agents.

13. The method of claim 11 wherein the first drug layer consists of the selected first therapeutic agent.

14. The method of claim 1 further comprising coupling the drug coated stent to a catheter.

15. The method of claim 1 wherein thickness of the second magnesium coating layer is sized to control drug elution from the second drug layer.

16. The method of claim 1 wherein thickness of the first magnesium coating layer is sized to control drug elution from the first drug layer.

* * * * *